United States Patent
Raciti et al.

(10) Patent No.: US 12,217,420 B2
(45) Date of Patent: Feb. 4, 2025

(54) SYSTEMS AND METHODS FOR PROCESSING ELECTRONIC IMAGES TO DETERMINE TESTING FOR UNSTAINED SPECIMENS

(71) Applicant: PAIGE.AI, Inc., New York, NY (US)

(72) Inventors: Patricia Raciti, New York, NY (US); Christopher Kanan, Pittsford, NY (US); Alican Bozkurt, New York, NY (US); Belma Dogdas, Ridgewood, NJ (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/933,156

(22) Filed: Sep. 19, 2022

(65) Prior Publication Data

US 2023/0020368 A1    Jan. 19, 2023

Related U.S. Application Data

(63) Continuation of application No. 17/547,695, filed on Dec. 10, 2021, now Pat. No. 11,481,899, which is a continuation of application No. 17/457,451, filed on Dec. 3, 2021, now Pat. No. 11,482,319.

(60) Provisional application No. 63/158,791, filed on Mar. 9, 2021.

(51) Int. Cl.
| | | |
|---|---|---|
| G06T 7/00 | (2017.01) | |
| G06N 3/045 | (2023.01) | |
| G06T 11/00 | (2006.01) | |
| G06V 10/77 | (2022.01) | |
| G16H 30/20 | (2018.01) | |

(52) U.S. Cl.
CPC .......... *G06T 7/0012* (2013.01); *G06N 3/045* (2023.01); *G06T 11/001* (2013.01); *G06V 10/7715* (2022.01); *G16H 30/20* (2018.01); *G06T 2207/30024* (2013.01)

(58) Field of Classification Search
CPC .............. G06T 7/0012; G06T 11/001; G06T 2207/30024; G16H 30/20; G06V 10/7715; G06N 3/045
See application file for complete search history.

(56) References Cited

U.S. PATENT DOCUMENTS

| | | | |
|---|---|---|---|
| 2019/0206056 A1* | 7/2019 | Georgescu | ............. G16H 50/20 |
| 2020/0226462 A1 | 7/2020 | Maddison et al. | |
| 2020/0258223 A1* | 8/2020 | Yip | .......................... G06T 7/11 |

(Continued)

*Primary Examiner* — Vu Le
*Assistant Examiner* — Winta Gebreslassie
(74) *Attorney, Agent, or Firm* — Bookoff McAndrews, PLLC

(57) ABSTRACT

A computer-implemented method may include receiving a collection of unstained digital histopathology slide images at a storage device and running a trained machine learning model on one or more slide images of the collection to infer a presence or an absence of a salient feature. The trained machine learning model may have been trained by processing a second collection of unstained or stained digital histopathology slide images and at least one synoptic annotation for one or more unstained or stained digital histopathology slide images of the second collection. The computer-implemented method may further include determining at least one map from output of the trained machine learning model and providing an output from the trained machine learning model to the storage device.

20 Claims, 5 Drawing Sheets

(56) References Cited

U.S. PATENT DOCUMENTS

2021/0064845 A1* 3/2021 Stumpe ................ G06V 20/695
2021/0090694 A1* 3/2021 Colley .................. G16H 15/00
2021/0145283 A1   5/2021 Bryant-Greenwood et al.

* cited by examiner

SYSTEMS AND METHODS FOR PROCESSING ELECTRONIC IMAGES TO DETERMINE TESTING FOR UNSTAINED SPECIMENS

RELATED APPLICATION

This patent application is a continuation of U.S. application Ser. No. 17/547,695, filed Dec. 10, 2021, which is a continuation of U.S. application Ser. No. 17/457,451, filed Dec. 3, 2021, which claims priority to U.S. Provisional Application No. 63/158,791, filed Mar. 9, 2021, all of which are hereby incorporated herein by reference in their entireties.

FIELD OF THE DISCLOSURE

Various embodiments of the present disclosure pertain generally to image processing methods. More specifically, particular embodiments of the present disclosure relate to systems and methods for analyzing unstained tissue specimens for additional testing.

BACKGROUND

Current workflows for genomic sequencing of a tumor have many inefficiencies. A workflow may require a pathologist to re-review materials to select the best slides/sections of tumor areas for sequencing, which may be challenging and time consuming. One of the major inefficiencies within the current workflow is that after selection of the appropriate block for testing, the prepared slides may be unstained. As such, it may be difficult for a technician to know precisely where to acquire samples from each unstained slide and to assess the quality of each slide.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for analysis of unstained tissue specimen for additional testing.

A computer-implemented method may include receiving a collection of unstained digital histopathology slide images at a storage device and running a trained machine learning model on one or more slide images of the collection to infer a presence or an absence of a salient feature. The trained machine learning model may have been trained by processing a second collection of unstained or stained digital histopathology slide images and at least one synoptic annotation for one or more unstained or stained digital histopathology slide images of the second collection. The computer-implemented method may further include determining at least one map from output of the trained machine learning model and providing an output from the trained machine learning model to the storage device.

A system for using a trained machine learning model for tissue analysis includes memory storing instructions, and at least one processor executing the instructions to perform a process. The process may include receiving a collection of unstained digital histopathology slide images at a storage device and running the trained machine learning model on one or more slide images of the collection to infer a presence or an absence of a salient feature. The trained machine learning model may have been trained by processing a second collection of unstained or stained digital histopathology slide images and at least one synoptic annotation for one or more unstained or stained digital histopathology slide images of the second collection. The process may include determining at least one map from output of the trained machine learning model and providing an output from the trained machine learning model to the storage device.

A non-transitory computer-readable medium storing instructions that, when executed by a processor, cause the processor to perform a method for using a trained machine learning model for tissue analysis. The method may include receiving a collection of unstained digital histopathology slide images at a storage device and running a trained machine learning model on one or more digital histopathology slide images to infer a presence or an absence of a salient feature. The trained machine learning model may have been trained by processing a second collection of unstained or stained digital histopathology slide images and at least one synoptic annotation for one or more unstained or stained digital histopathology slide images of the second collection. The method may include determining at least one map from output of the trained machine learning model and providing an output from the trained machine learning model to the storage device.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Figure 1A:
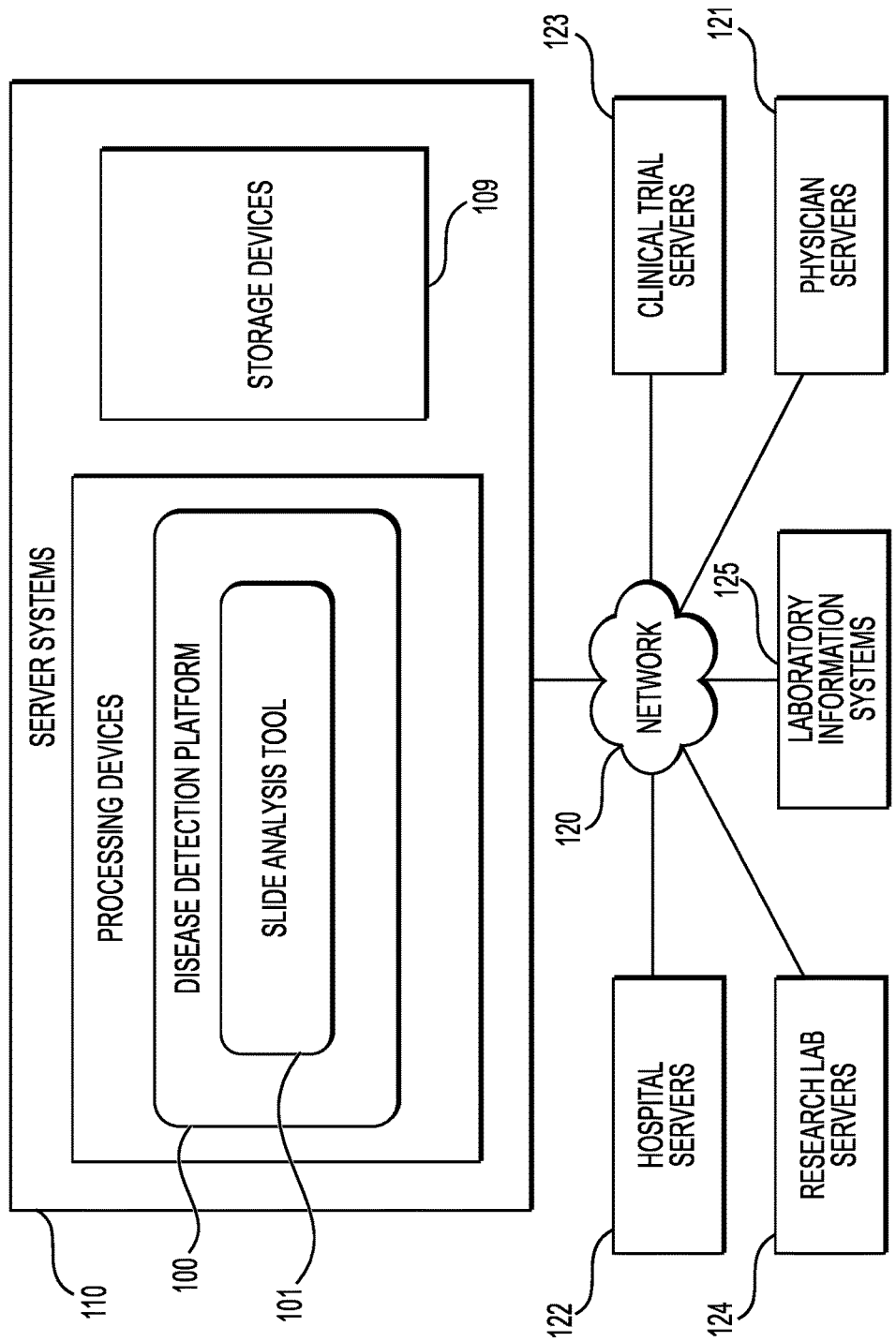
FIG. 1A illustrates an example block diagram of a system and network for analysis of an unstained tissue slide, according to certain embodiments of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

Molecular laboratories may evaluate a tumor genome using tissue samples from unstained formalin fixed paraffin embedded tissue (FFPE) slides or blood using next-generation sequencing (NGS) to identify mutations, fusions, or deletions at the gene level. This may be done to pinpoint the origin of the tumor, confer prognosis, guide treatment decisions (e.g., targeted therapies, immune-oncology therapies, or basket trials), and/or to evaluate minimal residual disease (MRD). While this may be relatively straightforward for blood samples, it is a complex multi-step process for FFPE samples.

For example, for FFPE, a workflow may begin with a primary diagnosis of a tumor from either biopsy or resection slides by a pathologist. The tissue specimens from a patient may be embedded into FFPE blocks and a portion of each block may be sliced to prepare slides, and those slides may be used to render the diagnosis, leaving the remainder of the FFPE block to be potentially used for genomic sequencing.

After primary diagnosis, the treating oncologist may request either a pan-tumor or a specific genetic test. The request may be delivered to the sign-out pathologist who may re-review the slides from each FFPE block that contains the most suitable sections of the tumor. To identify the most suitable tumor sections, the block for which the existing slides that have been cut which have the highest tumor purity, least necrosis, and/or least inflammation may be chosen. This step may be performed via manual re-review of slides and may be quite time consuming. After identifying the block, a number of unstained slides (e.g., 11 slides) from that block may be cut into the workflow for a pan-tumor NGS panel. The last slide in the block may then be stained and evaluated. For example, and in the case of a block of 11 slides, the eleventh slide may be stained with hematoxylin and eosin (H&E) and may be evaluated for residual tumor to help ensure the previous ten unstained slides have sufficient quantity of tumor. The remaining (e.g., 10) unstained slides may be sent to the molecular laboratory along with a requisition/form containing basic patient information (e.g., age, gender, topline diagnosis).

Upon arrival in the molecular lab, the first unstained slide may be stained with H&E, evaluated by a technician under a microscope for the precise location of the tumor, and then the tumor may be annotated by the technician using either a diamond tipped pencil or a marker. This location may be roughly marked on the remaining nine unstained slides such that a technician can "macro dissect" these areas rich in tumor from the slide. Macro dissection may include using a blade to scrape the unstained FFPE tissue from the surface of the slide and suctioning it such that the tissue can be macerated and deoxyribonucleic acid (DNA) extracted. Polymerase chain reaction (PCR) testing may then be performed on those tumor sections and the results may be fed through a robust bioinformatics data pipeline. A molecular pathologist may analyze the results and classify mutations into various tiers of clinical significance and action.

In some instances, there may be an insufficient quantity of tumor or the presence of large necrotic regions, which can result in the tissue being deemed insufficient for testing. If this occurs, the diagnosing pathologist may be alerted and asked to select a FFPE block that is likely to have more tumor for a second attempt at conducting molecular testing.

If there is sufficient tumor for molecular testing, then the molecular testing may be performed on the sample after being received by a lab. The lab may generate a comprehensive report that is sent back to the primary diagnosing pathologist, and this report may be appended to the original diagnostic report for subsequent review by the oncologist. This process generally may take two weeks, but another two weeks may be needed if there is an insufficient amount of the tumor. Thus, the process of evaluating and processing samples can be inaccurate, time consuming, and inconsistent, which wastes laboratory resources and results in slow or inaccurate diagnoses.

Certain embodiments described herein may provide for analysis of unstained tissue specimen for additional testing. In particular, certain embodiments may use artificial intelligence (AI) to identify samples from unstained slides and control the quality of each slide (or one or more of the slides). For example, the systems and methods of this disclosure may leverage AI techniques to detect cellular features that are necessary for pathological diagnosis, prognostic, and treatment decisions. Data and predictions may be aggregated and made available instantaneously (or with low latency) via any user interface (e.g., through a digital pathology viewing system, digital report, laboratory information system, etc.). Machine learning algorithms may rapidly or simultaneously assess a sample for adequacy, categorize the sample into diagnostic categories, and screen for the most likely molecular changes, thereby limiting the total molecular testing performed on a tumor and increasing the likelihood of a valid molecular result due to sufficient quantities of tumor. In this way, certain embodiments may provide for an efficient, consistent, and accurate way to evaluate and process samples, which may conserve resources of a laboratory and may improve a speed and accuracy of diagnosis.

After a block is chosen as the optimal block for testing, either by a pathologist or by an AI system, N slides (e.g., N=11) may be prepared from that block. Just the N−1 slide may then be stained, typically with H&E, to verify that the block is of sufficient quality. This has limitations, as the final slide may not be sufficient and it may not inform the technician doing the testing where on one or more unstained slides to test. Certain embodiments of the present disclosure may overcome this limitation by verifying that sufficient tumor is on one or more unstained slides and then indicating the spatial region on the one or more unstained slides that is optimal for testing. To process unstained slides, systems and methods of the present disclosure may be used to virtually stain the slides, e.g., to H&E, using an AI system that either takes as input a multispectral image of the slide or directly by learning from the unstained red, green, blue (RGB) image of the slide.

FIG. 1A illustrates an example block diagram of a system and network for analysis of unstained tissue slides, using machine learning, according to certain embodiments of the present disclosure. Specifically, FIG. 1A illustrates server systems 110 that includes various processing devices (e.g., a disease detection platform 100 that includes a slide analysis tool 101) and storage devices 109, a network 120, physician servers 121, hospital servers 122, clinical trial servers 123, research lab servers 124, and laboratory information systems 125.

The server systems 110 may include one or more interconnected systems of server devices (e.g., multiple interconnected datacenters or cloud networks, multiple interconnected systems within a datacenter or a cloud network, etc.). Server systems 110 may include one or more storage devices 109 (e.g., digital and/or electronic storage devices 109) for storing images and data received from at least one of the physician servers 121, the hospital servers 122, the clinical trial servers 123, the research lab servers 124, and/or the laboratory information systems 125. The server systems 110 may also include processing devices for processing images and data stored in the one or more storage devices 109. For example, the server systems 110 may include processing devices that are configured to implement the disease detection platform 100. The disease detection platform 100 may use the slide analysis tool 101 to analyze tissues in a whole slide image (WSI).

The server systems 110 may further include one or more machine learning tool(s) or capabilities. For example, the processing devices may include a machine learning tool for the disease detection platform 100 (e.g., the processing devices may run one or more trained machine learning models). In certain embodiments, a portion or all of the operations performed by the processing devices may be performed on a local processing device (e.g., a desktop computer, a laptop computer, a mobile phone, a tablet, etc.).

The network 120 may include one or more wired and/or wireless networks, such as the Internet, an intra-net, a cellular network (e.g., a Third Generation Partnership Project (3GPP) 3G network, 4G network 5G network, etc.), a wide area network (WAN), a local area network (LAN), a public land mobile network (PLMN), and/or the like. The network 120 may be connected to servers, e.g., at hospitals, laboratories, doctors' offices, etc. For example, the physician servers 121, the hospital servers 122, the clinical trial servers 123, the research lab servers 124, and/or the laboratory information systems 125, etc., may each be connected to the network 120, such as the Internet, through one or more computers, servers, and/or handheld mobile devices. According to an example embodiment of the present disclosure, the network 120 may also be connected to the server systems 110.

The physician servers 121, the hospital servers 122, the clinical trial servers 123, the research lab servers 124, and/or the laboratory information systems 125 may include one or more server devices (e.g., in a datacenter or distributed in a cloud network). The physician servers 121, the hospital servers 122, the clinical trial servers 123, the research lab servers 124, and/or the laboratory information systems 125 may create or otherwise obtain images of one or more patients' cytology specimen(s), histopathology specimen(s), slide(s) of the specimen(s), digitized images of the slide(s) of the specimen(s), or any combination thereof. The physician servers 121, the hospital servers 122, the clinical trial servers 123, the research lab servers 124, and/or the laboratory information systems 125 may also obtain any combination of patient-specific information, such as age, medical history, cancer treatment history, family history, past biopsy or cytology information, etc. The physician servers 121, the hospital servers 122, the clinical trial servers 123, the research lab servers 124, and/or the laboratory information systems 125 may transmit digitized slide images and/or patient-specific information to the server systems 110 over the network 120.

The physician servers 121, the hospital servers 122, the clinical trial servers 123, the research lab servers 124, and/or the laboratory information systems 125 may provide images of slides for review by a pathologist. In hospital settings, tissue type information may be stored in the laboratory information systems 125. In certain embodiments, cells in a WSI that share similar targets may be grouped without needing to access the laboratory information systems 125. Additionally, access to content stored by the laboratory information systems 125 may be limited due to its sensitive nature.

Figure 1B:
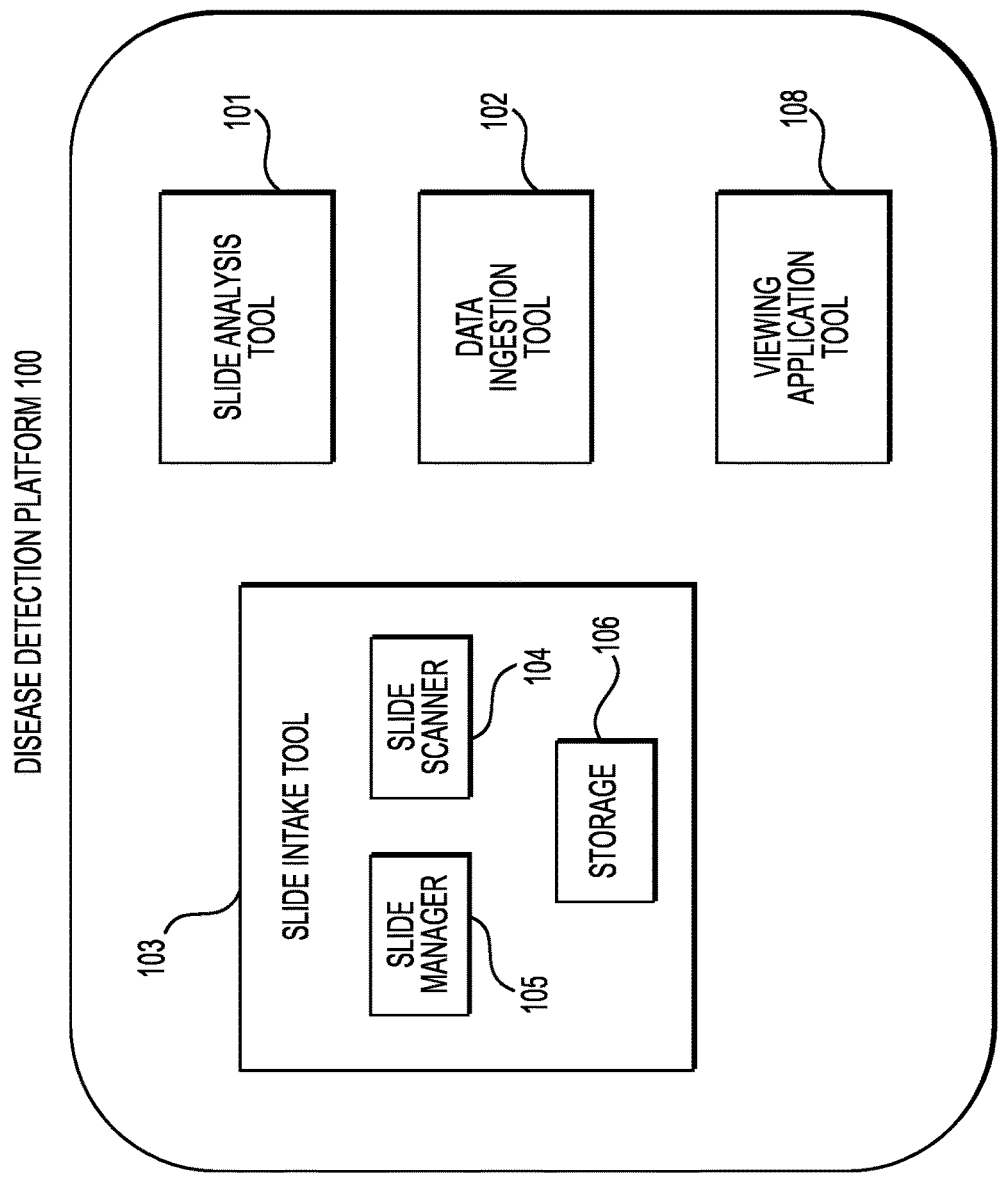
FIG. 1B illustrates an example block diagram of a disease detection platform of the system of FIG. 1A, according to certain embodiments of the present disclosure.

FIG. 1B illustrates an example block diagram of a disease detection platform 100 of the server systems 110 of FIG. 1A for analysis of unstained tissue slides, using machine learning, according to certain embodiments of the present disclosure. As illustrated in FIG. 1B, the disease detection platform 100 may include the slide analysis tool 101, a data ingestion tool 102, a slide intake tool 103 (which may include a slide scanner 104, a slide manager 105, and a storage 106), and a viewing application tool 108. The slide analysis tool 101 may include one or more computing devices capable of, e.g., grouping cells in a WSI that share similar targets. For example, the slide analysis tool 101 may transmit and/or receive digitized slide images and/or patient information to the server systems 110, the physician servers 121, the hospital servers 122, the clinical trial servers 123, the research lab servers 124, and/or the laboratory information systems 125 over the network 120.

The data ingestion tool 102 may include one or more computing devices capable of, e.g., facilitating a transfer of the digital pathology images to various tools, modules, components, and devices described herein that are used for classifying and processing the digital pathology images. The slide intake tool 103 may include one or more computing devices capable of, e.g., scanning pathology images and converting them into a digital form. For example, the slides may be scanned with the slide scanner 104, and the slide manager 105 may process the images on the slides into digitized pathology images and store the digitized images in the storage 106 (e.g., a digital or electronic storage device). The viewing application tool 108 may include one or more computing devices capable of, e.g., providing a user (e.g., a pathologist) with specimen property or image property information pertaining to digital pathology image(s). The information may be provided through various output interfaces (e.g., a screen, a monitor, a storage device, a web browser, etc.).

The server systems 110 (not illustrated in FIG. 1B) may store images and data received from the slide analysis tool 101, the data ingestion tool 102, the slide intake tool 103, the slide scanner 104, the slide manager 105, and/or the viewing application tool 108 (e.g., may store this information in the storage devices 109). The server systems 110 may process the images and data using the processing devices. The server systems 110 may further use one or more machine learning tool(s) or capabilities to process the images and data.

Figure 1C:
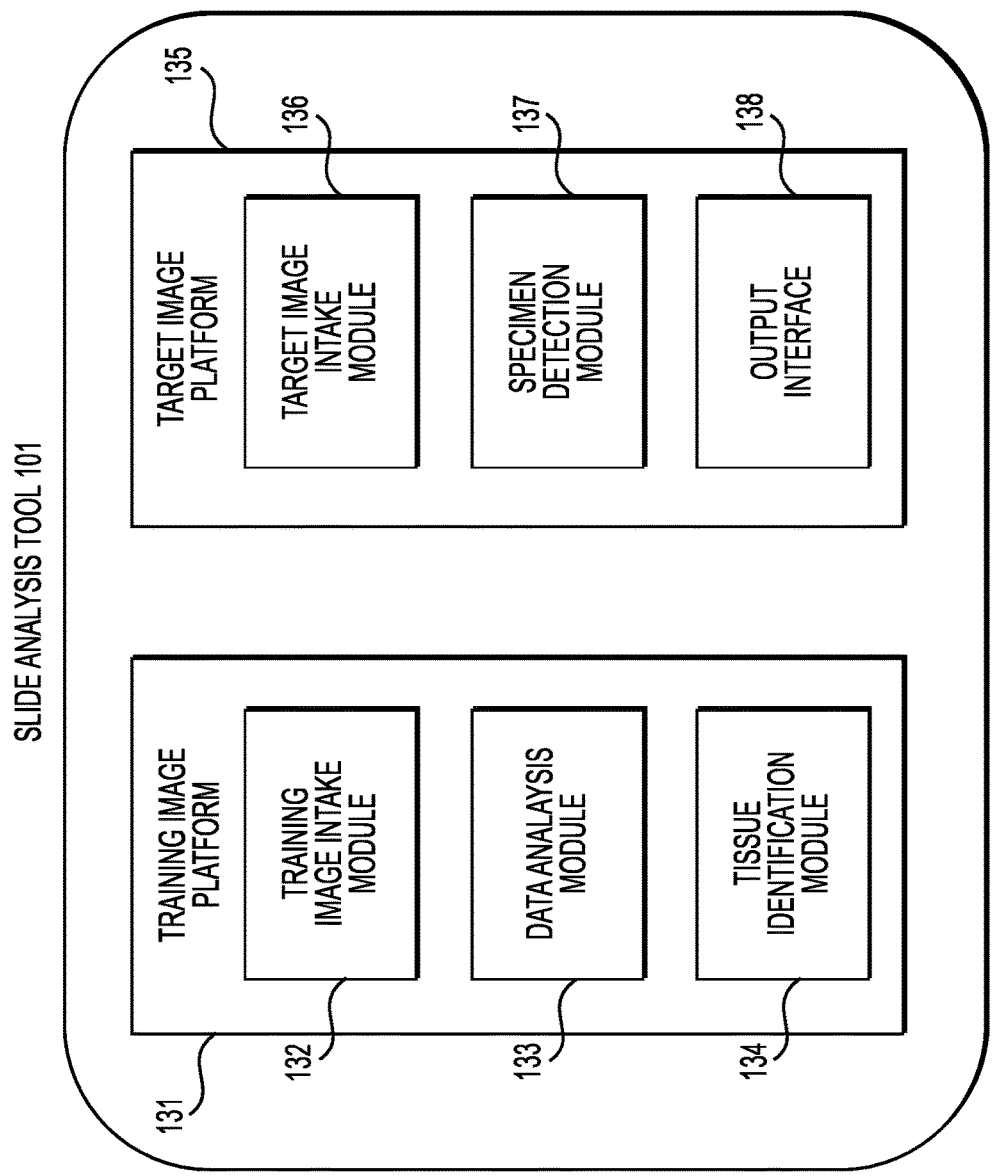
FIG. 1C illustrates an example block diagram of a slide analysis tool of the system of FIG. 1A, according to certain embodiments of the present disclosure.

FIG. 1C illustrates an example block diagram of a slide analysis tool 101 of the server systems 110 of FIG. 1A, according to certain embodiments of the present disclosure. The slide analysis tool 101 may include a training image platform 131 (e.g., that may include a training image intake module 132, a data analysis module 133, and a tissue identification module 134) and/or a target image platform 135 (e.g., that may include a target image intake module 136, a specimen detection module 137, and an output interface 138).

The training image platform 131 may include one or more computing devices capable of, e.g., creating or receiving training images that are used to train a machine learning model to effectively analyze and classify digital pathology images. For example, the training images may be received from the server systems 110, the physician servers 121, the hospital servers 122, the clinical trial servers 123, the research lab servers 124, and/or the laboratory information systems 125. Images used for training may be obtained from real sources (e.g., humans, animals, etc.) or may come from synthetic sources (e.g., graphics rendering engines, three dimensional (3D) models, etc.). Examples of digital pathology images may include (a) digitized slides stained with a variety of stains, such as H&E, Hematoxylin alone, immunohistochemistry (IHC), molecular pathology, etc.; and/or (b) digitized tissue samples from a 3D imaging device, such as microcomputed tomography (microCT).

The training image intake module 132 may include one or more computing devices capable of, e.g., creating, receiving, or analyzing a dataset comprising one or more training datasets corresponding to one or more health variables and/or one or more data variables. For example, the training datasets may be received from the server systems 110, the physician servers 121, the hospital servers 122, the clinical trial servers 123, the research lab servers 124, and/or the laboratory information systems 125. This dataset may be kept on a digital and/or electronic storage device. The data analysis module 133 may include one or more computing devices capable of, e.g., identifying whether a set of individual cells belong to a cell of interest or a background of a digitized image. The tissue identification module 134 may include one or more computing devices capable of, e.g., analyzing digitized images and determining whether an individual cell in the cytology sample needs further analysis. Upon identification that an individual cell needs further analysis, the tissue identification module may trigger an alert to a user.

The target image platform 135 may include one or more computing devices capable of, e.g., receiving a target image and applying a machine learning model to the received target image to determine a characteristic of a target data set. For example, the target data may be received from the server systems 110, the physician servers 121, the hospital servers 122, the clinical trial servers 123, the research lab servers 124, and/or the laboratory information systems 125. The target image intake module 136 may include one or more computing devices capable of, e.g., receiving a target dataset corresponding to a target health variable or a data variable. Specimen detection module 137 may include one or more computing devices capable of, e.g., applying a machine learning model to the target dataset to determine a characteristic of the target health variable or a data variable. For example, the specimen detection module 137 may detect a trend of the target relationship. The specimen detection module 137 may also apply the machine learning model to the target dataset to determine a quality score for the target dataset. Further, the specimen detection module 137 may apply the machine learning model to the target images to determine whether a target element is present in a determined relationship.

The output interface 138 may include one or more computing devices capable of, e.g., outputting information about the target data and the determined relationship (e.g., to a screen, monitor, storage device, web browser, etc.).

Figure 2:
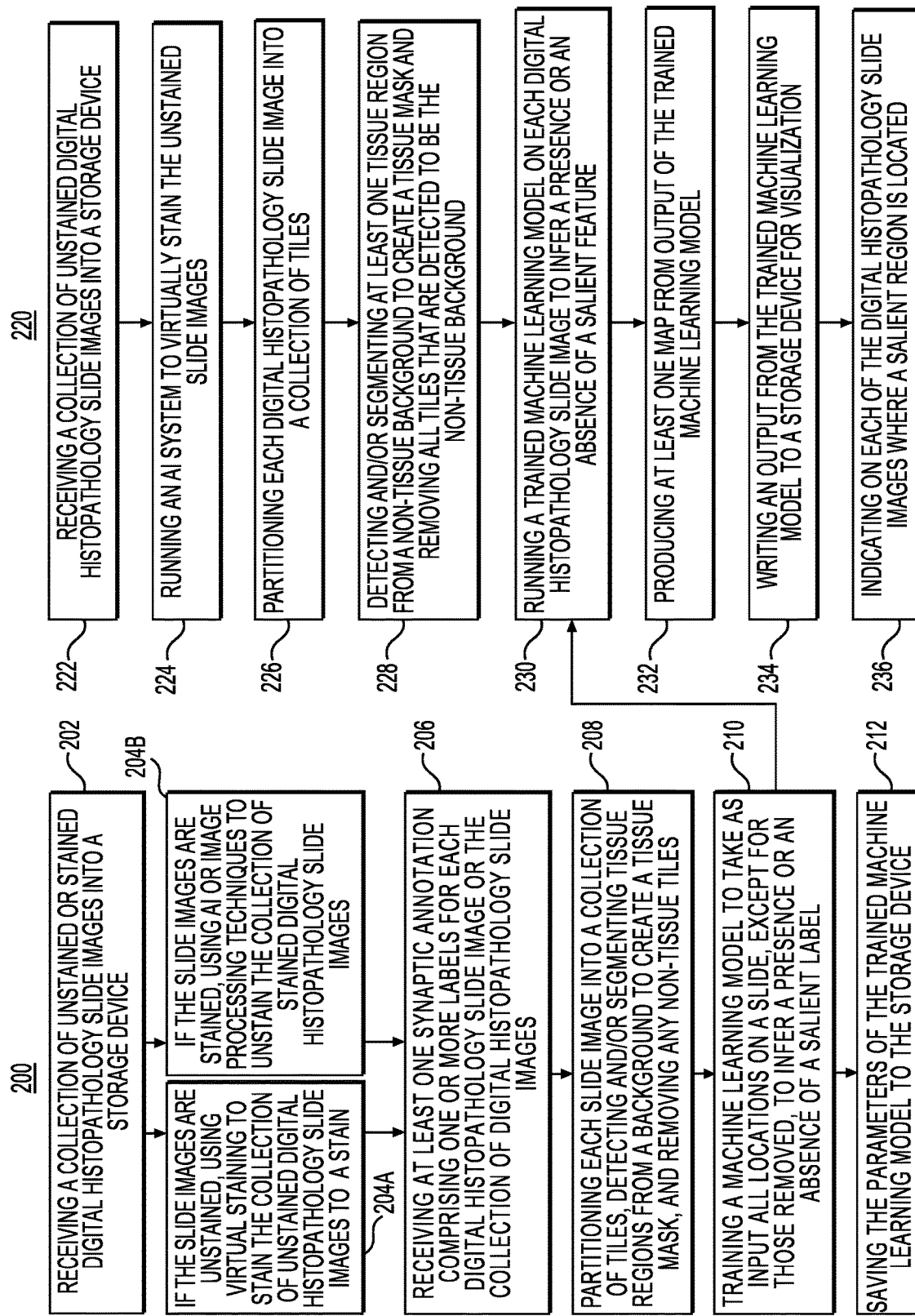
FIG. 2 is a flowchart illustrating example methods of training and using a machine learning model for tissue analysis, according to certain embodiments of the present disclosure.

FIG. 2 is a flowchart illustrating example methods 200 and 220 of training and using a machine learning model for tissue analysis, according to certain embodiments of the present disclosure. The methods 200 and 220 may be used to process unstained slides. For example, example methods 200 and 220 (e.g., steps 202-212 and steps 222-236, respectively) may be performed by the slide analysis tool 101 automatically or in response to a request from a user (e.g., a physician, pathologist, etc.) via the disease detection platform 100.

According to an embodiment, the example method 200 for training a machine learning model for tissue analysis may include one or more of the following steps. In step 202, the method 200 may include receiving a collection of unstained or stained digital histopathology slide images into a storage device (e.g., hard drive, network drive, cloud storage, random-access memory (RAM), etc.). In step 204A, the method 200 may include, if the slides images are unstained, using virtual staining to stain the collection of unstained digital histopathology slide images to a stain (e.g., H&E). In step 204B, the method 200 may include, if the slide images are stained, using AI or image processing techniques to un-stain the collection of stained digital histopathology slide images. Virtual unstaining may enable large repositories of previously stained slides to be used for training.

In step 206, the method 200 may include receiving at least one synoptic annotation comprising one or more labels for each digital histopathology slide image (or one or more slide image) or the collection of digital histopathology slide images. These labels may be at the pixel-level, tile-level, slide-level, and/or part specimen-level. The labels may be binary (or multi-label binary), categorical, ordinal, or real-valued. These labels may indicate the presence or absence of the salient attribute for testing, e.g., the presence of invasive cancer. Such steps may be performed in accordance with U.S. application Ser. No. 17/313,617, which is incorporated herein by reference. In step 208, the method 200 may include partitioning each slide image (or one or more slide images) into a collection of tiles, detecting and/or segmenting tissue regions from a background to create a tissue mask, and removing any non-tissue tiles. The detecting and segmenting may be performed using a variety of methods including, but not limited to, threshold-based methods (e.g., based on color/intensity, based on texture features, Otsu's method, etc.) followed by running the connected components algorithm; or segmentation algorithms (e.g., k-means, graph cuts, a mask region-based convolutional neural network (R-CNN), etc.).

In step 210, the method 200 may include training a machine learning model to take as input all (or one or more) locations on a slide, except for those removed in step 208, to infer a presence or an absence of a salient label. The model may be a support-vector machine (SVM), convolutional neural network (CNN), recurrent neural network (RNN), transformer, graph neural network (GNN), multi-layer perceptron (MLP), relationship network, fully convolutional semantic segmentation neural network, fully-convolutional instance segmentation network (e.g., mask R-CNN), object detection network (e.g., faster R-CNN), etc. In step 212, the method 200 may include saving the parameters of the trained machine learning model to a storage device.

The example method 220 for using a machine learning model for tissue analysis may include one or more of the following steps. In step 222, the method may include receiving a collection of unstained digital histopathology slide images into a storage device (e.g., hard drive, network drive, cloud storage, random access memory (RAM), etc.). In step 224, the method 220 may include running an AI system to virtually stain the unstained slide images. In step 226, the method 220 may include partitioning each digital histopathology slide image (or one or more slide images) into a collection of tiles. In step 228, the method 220 may include detecting and/or segmenting at least one tissue region from a non-tissue background to create a tissue mask and removing all (one or more) tiles that are detected to be the non-tissue background. This may be performed using a variety of methods, including but not limited to: threshold-based methods (e.g., based on color/intensity, based on texture features, Otsu's method, etc.) followed by running the connected components algorithm; or segmentation algorithms (e.g., k-means, graph cuts, a mask R-CNN, etc.).

In step 230, the method 220 may include running a trained machine learning model on each digital histopathology slide image (or one or more slide images) to infer a presence or an absence of a salient feature. In certain embodiments, the trained machine learning model may be the machine learning model trained in step 210 of the method 200. In step 232, the method 220 may include producing or otherwise determining at least one map from output of the trained machine learning model. If certain embodiments just output the presence or absence of the attribute, this may be performed using introspection techniques such as class activation mapping (CAM) and gradient-weighted CAM (GradCAM) to produce a heat map, and then the heat map may be processed using a threshold to determine where the salient tissue is located. If certain embodiments produce instance/semantic segmentations, then these outputs may be used directly to produce a map. If certain embodiments produce detection regions (e.g., Faster R-CNN), then these windows may be used directly to indicate the location.

In step 234, the method 220 may include writing or otherwise providing an output from the trained machine learning model to a storage device for visualization. The visualization may be performed by a technician to indicate where to sample and to identify whether adequate or inadequate tissue is present on any of the slides. Alternatively, the visualization may be performed using image processing techniques prior to writing an output to the storage device (e.g., an image processing technique may be used to determine whether adequate or inadequate tissue is present on a slide image). In step 236, the method 220 may include indicating on each of the digital histopathology slide images (or one or more slide images) where a salient region is located. For example, a marking, icon, etc. may be digitally applied to the slide images as the indication. This information may be used differently in different use cases. For macro dissection, contours around the salient regions may show a user the optimal places to scrape. For tissue microarrays, spatial information for multiple consecutive slides in a block and the optimal trajectory can be calculated and displayed to the technician. If none of the unstained slides have salient tissue, a new block may be selected for testing.

Certain embodiments described herein may be implemented in particular contexts. For example, certain embodiments may be implemented in a workflow for a continuous recurrence score for invasive breast cancer. In this context, after invasive breast cancer is detected, it is common to perform a genomic assay of the tumor to determine whether to forgo additional treatment, to give the patient endocrine (hormone) therapy, to give the patient adjuvant chemotherapy, or to give the patient some other therapy. These tests may assess the risk of recurrence and metastasis of disease after excising the primary tumor using a continuous scoring system. The tests may evaluate genomic information that relates to proliferation, invasion, metastasis, stromal integrity, and/or angiogenesis.

The EndoPredict (EPclin) test may be based on ribonucleic acid (RNA) expression of 12 genes and may combine this genomic information with additional clinical features to predict the 10-year distant recurrence (DR) rate of the disease. In this regard, the EPclin test may assign a score between 1 and 6, with 6 indicating a high risk of recurrence and 1 indicting a low risk of recurrence. Another example test may be MammaPrint, which may be a 70-gene assay that uses formalin-fixed-paraffin-embedded (FFPE) or fresh tissue. This test may then may use RNA isolated from the tumor sample to predict a continuous score with values greater than 0 indicating low risk of cancer recurrence and values less than 0 indicating a higher risk of recurrence. This may suggest that adjuvant chemotherapy is needed.

Another example test is the Breast Cancer Index (BCI) test, which may analyze seven genes to predict cancer recurrence. This test may produce two scores: the BCI Prognostic score, which may estimate the likelihood of the cancer returning five to ten years after diagnosis on a continuous scale of 0 to 10, with a score of 5.1 to 10 indicating a high risk of recurrence. The BCI Predictive score may estimate the likelihood of benefit from taking endocrine therapy for five additional years, for a total of ten years of endocrine therapy.

The Oncotype DX Recurrence Score is another such assay, which may be based on the expression of 21 genes within the tumor. This score may produce a number between 0 to 100 to indicate the risk of cancer recurrence, with a score of greater than 31 indicating a high risk of metastasis and the need for adjuvant chemotherapy with endocrine therapy, a score of 26 to 30 indicating uncertain benefit for adjuvant chemotherapy when used with endocrine therapy, and a score less than 26 indicating that endocrine therapy alone could suffice for treatment after surgery.

The Prosigna Breast Cancer Prognostic Gene Signature Assay (i.e., the PAM50 gene signature) may use RNA from FFPE samples to estimate the risk of distant recurrence for hormone receptor positive breast cancer. This technique may produce a continuous score from 0 to 100, with a higher score indicating a greater risk of recurrence to guide treatment decisions.

Another example context in which certain embodiments may be implemented may include a workflow for continuous score for a recurrence of non-invasive breast cancer. For example, following diagnosis of non-invasive breast cancer, adjuvant treatment may be needed after a patient has a lumpectomy or mastectomy. This treatment may include endocrine therapy or radiation treatment to reduce the risk of recurrence, but these treatments may have negative side effects. To determine the benefit a patient may have from these treatments, genomic assays have been developed.

One common form of non-invasive breast cancer is ductal carcinoma in situ (DCIS). One genomic test for determining treatment options for DCIS may include Oncotype DX DCIS, which may be a 12-panel genomic test. This test may produce a continuous score from 0 to 100 to determine the risk of breast cancer recurrence, with higher values indicating greater need for adjuvant treatment to prevent recurrence.

Another example context in which certain embodiments may be implemented may include a workflow for a continuous score for a prostate cancer treatment recommendation. For example, to diagnose prostate cancer, men may ordinarily receive a prostate biopsy. The biopsy sample may then be processed and visually reviewed by a pathologist to determine the presence and severity of disease. However, prostate cancer treatments, e.g., removal of the prostate, hormone therapy, and/or radiation therapy, can have a negative impact on a man's quality of life, and some patients may not need aggressive treatment.

An alternative to just using pathologic assessment of prostate tissue samples is to predict tumor aggressiveness using genomic assays. For example, the Oncotype DX Genomic Prostate Score may evaluate 17 genes to determine prostate cancer aggressiveness on a continuous score from 0 to 100. Patients with values closer to 0 may have active surveillance recommended whereas patients with higher scores may have immediate, aggressive treatment to reduce the risk of an adverse outcome (e.g., death or metastasis). Another test may include the Prolaris assay that combines genomic assessment with other measurements to determine a continuous score for if a man can choose active surveillance for prostate cancer instead of aggressive treatment, where a higher score indicates the aggressiveness of the cancer.

Another example context in which certain embodiments may be implemented may include a workflow for a continuous score for a likelihood of malignancy. For example, tumors are abnormal masses of cells, which can be benign or malignant. A benign tumor lacks the ability to metastasize or invade surrounding tissue, whereas a malignant tumor can do so. In some situations, pathological assessment may not suffice for determining if a tumor is malignant or benign. In this scenario, a continuous score can be used to better make the determination.

For example, the Myriad myPath Melanoma test may measures 23 genes associated with cell differentiation, cell signaling, and immune response signaling to produce a continuous score on a scale of approximately −16 to 10. Scores greater than zero may indicate that the skin tumor is likely to be malignant and that aggressive treatment is needed, whereas a score of less than −2 may indicate that the tumor is likely benign.

Systems and methods of the present disclosure may verify that the unstained slides have sufficient tumor and may highlight the tumor location for the above-described tests in the various above-described contexts. For example, there may have to be different amounts of tumor for different tests and the trained machine learning model described above may evaluate the amount of tumor present in the unstained slide images to determine whether the unstained slide images show a sufficient amount of tumor for one or more of the above-described tests (e.g., the machine learning model may be trained using synoptic annotations that include labels of tests for which amounts of tumor shown in the other collection of unstained or stained digital histopathology slide images are sufficient). The trained machine learning model may then indicate on each of the digital histopathology slide images (or on one or more slide images) the tumor location, e.g., in a manner similar to that at step 236 of the method 220. Additionally, or alternatively, the trained machine learning model may output, based on determining that the one or more digital histopathology slide images do not show a sufficient amount of tumor, information indicating an amount by which the amount of tumor is insufficient. Additionally, or alternatively, the trained machine learning model may generate a recommendation for a specific test, of one or more tests, based on determining that the one or more digital histopathology slide images show a sufficient amount of tumor. For example, the trained machine learning model may generate a recommendation for performing a particular test if the amount of tumor shown in the slide images is sufficient for multiple tests.

Figure 3:
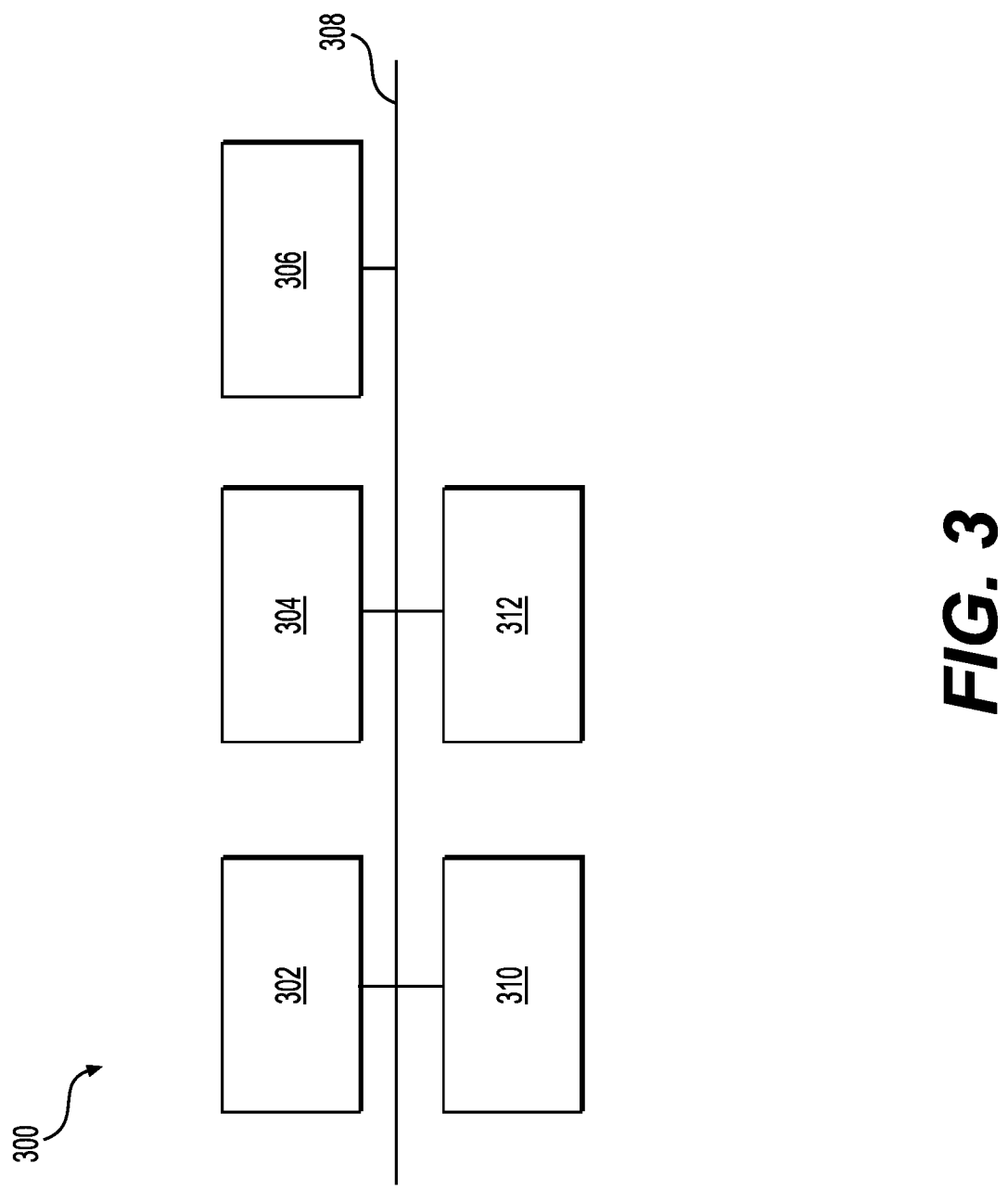
FIG. 3 illustrates an example computing device, according to certain embodiments of the present disclosure.

FIG. 3 illustrates an example computing device 300, according to certain embodiments of the present disclosure. In particular, FIG. 3 is a simplified functional block diagram of a computing device 300 that may be configured as a device for executing the methods of FIG. 2. For example, the computing device 300 may be configured as the disease detection platform 100 (or tools thereof illustrated in FIG. 1B), the slide analysis tool 101 (or platforms or modules thereof illustrated in FIG. 1C), the server systems 110, the physician servers 121, the hospital servers 122, the clinical trial servers 123, the research lab servers 124, the laboratory information systems 125, and/or another device or system according to certain embodiments described herein. In various embodiments, any of the devices or systems described herein may be the computing device 300 illustrated in FIG. 3 and/or may include one or more of the computing devices 300.

As illustrated in FIG. 3, the computing device 300 may include a processor 302, a memory 304, an output component 306, a communication bus 308, an input component 310, and a communication interface 312. The processor 302 may include a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some embodiments, the processor 302 includes one or more processors capable of being programmed to perform a function. The memory 304 may include a random access memory (RAM), a read only memory (ROM), and/or another type of dynamic or static storage device (e.g., a flash memory, a magnetic memory, and/or an optical memory) that stores information and/or instructions for use by the processor 302.

The output component 306 may include a component that provides output information from the computing device 300 (e.g., a display, a speaker, and/or one or more light-emitting diodes (LEDs)). The communication bus 308 may include a component that permits communication among the components of the computing device 300. The input component 310 may include a component that permits the computing device 300 to receive information, such as via user input (e.g., a touch screen display, a keyboard, a keypad, a mouse, a button, a switch, and/or a microphone). Additionally, or alternatively, the input component 310 may include a sensor for sensing information (e.g., a global positioning system (GPS) component, an accelerometer, a gyroscope, and/or an actuator). The communication interface 312 may include a transceiver-like component (e.g., a transceiver and/or a separate receiver and transmitter) that enables the computing device 300 to communicate with other devices, such as via a wired connection, a wireless connection, or a combination of wired and wireless connections. The communication interface 312 may permit the computing device 300 to receive information from another device and/or provide information to another device. For example, the communication interface 312 may include an Ethernet interface, an optical interface, a coaxial interface, an infrared interface, a radio frequency (RF) interface, a universal serial bus (USB) interface, a wireless local area network interface, a cellular network interface, and/or the like.

As noted above, the computing device 300 illustrated in FIG. 3 may perform one or more processes described herein. The computing device 300 may perform these processes based on the processor 302 executing software instructions stored by a non-transitory computer-readable medium, such as the memory 304 and/or another storage component. For example, the storage component may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive. A computer-readable medium is defined herein as a non-transitory memory device. A memory device includes memory space within a single physical storage device or memory space spread across multiple physical storage devices.

Software instructions may be read into the memory 304 and/or a storage component from another computer-readable medium or from another device via the communication interface 312. When executed, software instructions stored in the memory 304 and/or the storage component may cause the processor 302 to perform one or more processes described herein. Additionally, or alternatively, hardwired circuitry may be used in place of or in combination with software instructions to perform one or more processes described herein. Thus, embodiments described herein are not limited to any specific combination of hardware circuitry and software.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method, comprising:
   receiving a collection of unstained digital histopathology slide images;
   providing one or more unstained digital histopathology slide images of the collection to a trained machine learning model to infer a presence or an absence of a salient feature,
   the trained machine learning model having been trained by processing a second collection of unstained and/or stained digital histopathology slide images and at least one synoptic annotation for one or more unstained and/or stained digital histopathology slide images of the second collection, wherein the processing comprises:
      virtually staining one or more unstained digital histopathology slide images of the second collection to a stain or using an image processing technique to un-stain one or more stained digital histopathology slide images of the second collection; and
      training a machine learning model to take as input one or more locations on a slide image to infer a presence of a salient label;
   determining at least one map based on an output of the trained machine learning model, wherein the at least one map produces detection regions; and
   utilizing the at least one map, to determine where the salient feature is located, in one or more tests related to the collection of unstained digital histopathology slide images.

2. The computer-implemented method of claim 1, wherein one or more scores indicating one or more characteristics of a disease are output based on the one or more tests, and wherein the one or more characteristics of the disease include a likelihood of recurrence of the disease or a response of the disease to a treatment.

3. The computer-implemented method of claim 1, wherein the one or more tests include a molecular test or a genomic assay.

4. The computer-implemented method of claim 1, wherein the one or more tests are associated with providing a continuous recurrence score for invasive breast cancer.

5. The computer-implemented method of claim 1, wherein the one or more tests are associated with providing a continuous score for recurrence of non-invasive breast cancer.

6. The computer-implemented method of claim 1, wherein the one or more tests are associated with providing a continuous score for a likelihood of malignancy of a tumor.

7. The computer-implemented method of claim 1, further comprising, prior to utilizing the at least one map:
   determining whether the unstained slide images show a sufficient amount of salient features for the one or more tests, wherein training the machine learning model further includes using synoptic annotations that include labels of tests for which amounts of salient feature shown in the second collection of unstained and/or stained digital histopathology slide images are sufficient; and;
   generating a recommendation for a specific test, of one or more tests, based on determining that the one or more slide images of the collection show a sufficient amount of the salient feature.

8. The computer-implemented method of claim 1, further comprising, prior to utilizing the at least one map:
   determining whether the unstained slide images show a sufficient amount of salient features for the one or more tests, wherein training the machine learning model further includes using synoptic annotations that include labels of tests for which amounts of salient feature shown in the second collection of unstained and/or stained digital histopathology slide images are sufficient; and
   outputting information indicating an amount by which the amount of salient feature is insufficient, based on determining that no slide images in the collection of unstained digital histopathology slide images contain salient tissue.

9. The computer-implemented method of claim 1, wherein the determining of the at least one map further comprises:
   determining the at least one map using an introspection technique to produce at least one heat map as the at least one map.

10. The computer-implemented method of claim 2, further comprising:
   determining a treatment for the disease based on the one or more scores.

11. The computer-implemented method of claim 8, further comprising:
   selecting another collection of unstained digital histopathology slide images for testing, based on the information indicating an amount by which the amount of salient feature is insufficient.

12. A system for using a trained machine learning model for tissue analysis includes memory storing instructions, and at least one processor executing the instructions to perform operations comprising:
   receiving a collection of unstained digital histopathology slide images;
   running the trained machine learning model on one or more unstained digital histopathology slide images of the collection to infer a presence or an absence of a salient feature,
   wherein the trained machine learning model has been trained by processing a second collection of unstained and/or stained digital histopathology slide images and at least one synoptic annotation for one or more unstained and/or stained digital histopathology slide images of the second collection, wherein the processing comprises:
      virtually staining one or more unstained digital histopathology slide images of the second collection to a stain or using an image processing technique to un-stain one or more stained digital histopathology slide images of the second collection; and
      training a machine learning model to take as input one or more locations on a slide image to infer a presence of a salient label;
   determining at least one map based on output of the trained machine learning model, wherein the at least one map produces detection regions; and
   utilizing the at least one map, to determine where the salient feature is located, in one or more tests related to the collection of unstained digital histopathology slide images.

13. The system of claim 12, wherein one or more scores indicating one or more characteristics of a disease are output based on the one or more tests, and wherein the one or more characteristics of the disease include a likelihood of recurrence of the disease or a response of the disease to a treatment.

14. The system of claim 12, wherein the one or more tests are associated with providing a continuous recurrence score for invasive breast cancer.

15. The system of claim 12, wherein the one or more tests are associated with providing a continuous score for recurrence of non-invasive breast cancer.

16. The system of claim 13, the operations further comprising:
   determining a treatment for the disease based on the one or more scores.

17. A non-transitory computer-readable medium storing instructions that, when executed by a processor, cause the processor to perform operations for using a trained machine learning model for tissue analysis, the operations comprising:
   receiving a collection of unstained digital histopathology slide images;
   running a trained machine learning model on one or more unstained digital histopathology slide images to infer a presence or an absence of a salient feature,
   wherein the trained machine learning model has been trained by processing a second collection of unstained and/or stained digital histopathology slide images and at least one synoptic annotation for one or more unstained and/or stained digital histopathology slide images of the second collection, wherein the processing comprises:
      virtually staining one or more unstained digital histopathology slide images of the second collection to a stain or using an image processing technique to un-stain one or more stained digital histopathology slide images of the second collection; and
      training a machine learning model to take as input one or more locations on a slide image to infer a presence of a salient label;
   determining at least one map based on output of the trained machine learning model, wherein the at least one map produces detection regions; and
   utilizing the at least one map, to determine where the salient feature is located, in one or more tests related to the collection of unstained digital histopathology slide images.

18. The non-transitory computer-readable medium of claim 17, wherein the one or more tests include a molecular test or a genomic assay.

19. The non-transitory computer-readable medium of claim 17, wherein the one or more tests are associated with providing a continuous score for a likelihood of malignancy of a tumor.

20. The non-transitory computer-readable medium of claim 17, the operations further comprising:
   determining whether the unstained slide images show a sufficient amount of salient features for the one or more tests, wherein training the machine learning model further includes using synoptic annotations that include labels of tests for which amounts of salient feature shown in the second collection of unstained and/or stained digital histopathology slide images are sufficient; and
   generating a recommendation for a specific test, of the one or more tests, based on determining that the one or more slide images of the collection show a sufficient amount of salient feature.

* * * * *